United States Patent
Allmendinger et al.

(10) Patent No.: US 8,218,719 B2
(45) Date of Patent: Jul. 10, 2012

(54) COMPUTERIZED METHOD AND PROCESSOR FOR SELECTING ACQUISITION CONFIGURATIONS TO OBTAIN X-RAY COMPUTED TOMOGRAPHY DATA

(75) Inventors: Thomas Allmendinger, Forchheim (DE); Stefan Reichelt, Bamberg (DE); Carsten Thierfelder, Pinzberg (DE)

(73) Assignee: Siemens Aktiengesellschaft, Munich (DE)

( * ) Notice: Subject to any disclaimer, the term of this patent is extended or adjusted under 35 U.S.C. 154(b) by 52 days.

(21) Appl. No.: 12/953,735

(22) Filed: Nov. 24, 2010

(65) Prior Publication Data
US 2011/0129056 A1  Jun. 2, 2011

(30) Foreign Application Priority Data
Dec. 2, 2009  (DE) .......................... 10 2009 056 721

(51) Int. Cl.
*A61B 6/03* (2006.01)
(52) U.S. Cl. ................................ 378/8; 378/4; 378/210
(58) Field of Classification Search ........... 378/4; 705/3
See application file for complete search history.

(56) References Cited

U.S. PATENT DOCUMENTS

2005/0267348 A1 * 12/2005 Wollenweber et al. ....... 600/407
2007/0162159 A1    7/2007 Ladenburger

* cited by examiner

*Primary Examiner* — Edward Glick
*Assistant Examiner* — John Corbett
(74) *Attorney, Agent, or Firm* — Schiff Hardin LLP

(57) ABSTRACT

In a method to assist in the selection of an acquisition configuration from a set of adjustable acquisition configurations for the acquisition of x-ray projections of the heart of a patient with a computed tomography apparatus to examine the heart of the patient, the which method is based on an examination type to be specified. At least two acquisition configurations for the specified examination type (which acquisition configurations can be adjusted at the computed tomography apparatus) are considered for which at least one probability density function is respectively kept ready that was determined for the respective acquisition configuration for a specific variable pertaining to a person and/or for the x-ray dose to be applied to the person. Using the at least two probability density functions, the acquisition configuration that is best suited for the examination of the heart of the patient according to the specified examination type is determined from the at least two adjustable acquisition configurations under consideration, based on at least one determined variable to be specified and pertaining to the current patient to be examined and/or based on a value pertaining to the applied x-ray dose. The invention also concerns a computed tomography apparatus operable according to such a method and a storage medium encoded with programming instructions for implementing such a method.

11 Claims, 3 Drawing Sheets

Probability

HR

Probability

HRV

Probability

A

Probability

Supplementary unit

Probability

HR

Probability

HRV

Probability

A

Probability

Supplementary unit

COMPUTERIZED METHOD AND PROCESSOR FOR SELECTING ACQUISITION CONFIGURATIONS TO OBTAIN X-RAY COMPUTED TOMOGRAPHY DATA

BACKGROUND OF THE INVENTION

1. Field of the Invention

The invention concerns a method to support the selection of an acquisition configuration from a set of adjustable acquisition configurations for the acquisition of x-ray projections of the heart of a patient with an x-ray computed tomography apparatus to examine the heart of the patient. The invention moreover concerns an x-ray computed tomography apparatus to execute the method and non-transitory computer-readable storage medium encoded with programming instructions for implementing such a method.

2. Description of the Prior Art

Computed tomography apparatuses which are used for the imaging of the heart of a patient presently offer a plethora of adjustment possibilities for the acquisition of x-ray projections of the heart, which form the basis for the reconstruction of slice images or of a volume data set of the heart. The number of adjustment possibilities offers the user of such a computed tomography apparatus a high degree of freedom. The experienced user also can purposefully use these adjustment possibilities to achieve as optimal an image quality as possible for the slice images or 3D images to be reconstructed. However, inexperienced users of such computed tomography apparatuses perceive the large number of adjustment possibilities to be confusing. The achievable image quality in reconstructed slice images or 3D images therefore depends not only on the computed tomography apparatus itself but also on the experience of the respective user.

SUMMARY OF THE INVENTION

An object of the present invention is to provide a method, a computed tomography apparatus and a data medium of the aforementioned type such that the user of a computed tomography apparatus is better assisted in the adjustment of the computed tomography apparatus for the acquisition of x-ray projections of the heart of a patient.

According to the invention, this object is achieved by a method to assist in the selection of an acquisition configuration from a set of adjustable acquisition configurations for the acquisition of x-ray projections of the heart of a patient with a computed tomography apparatus to examine the heart of the patient; in which, based on an examination type to be specified, at least two acquisition configurations for the specified examination type (which acquisition configurations can be adjusted at the computed tomography apparatus) are considered for which at least one probability density function is respectively kept ready that was determined for the respective acquisition configuration for a specific variable pertaining to a person and/or for the x-ray dose to be applied to the person; and in which—using the at least two probability density functions—the acquisition configuration that is best suited for the examination of the heart of the patient according to the specified examination type is determined from the at least two adjustable acquisition configurations under consideration, based on at least one determined variable to be specified and pertaining to the current patient to be examined and/or based on a value pertaining to the applied x-ray dose.

As used herein an "adjustable acquisition configuration" or an "adjustable scan protocol" means a predetermined set of setting parameters for a computed tomography apparatus to acquire 2D x-ray projections, which acquisition configuration or, respectively, scan protocol possesses, the for example the acquisition mode (thus sequence or spiral, for example); the width of the pulsing window; the position of the pulsing window relative to the cardiac cycle; the tube voltage; the pitch given spirals, etc. Multiple such adjustable acquisition configurations are stored for selection, for example in a memory of the computed tomography apparatus. If one of the acquisition configurations is selected, the adjustment of the setting parameters at the computed tomography apparatus advantageously ensues automatically without additional user interaction. However, this does not mean that the user cannot nevertheless independently change individual parameters.

Multiple probability density functions are advantageously present in a memory of the computed tomography apparatus for every single adjustable acquisition configuration. Probability density functions normally exist that have been specifically determined for a specific variable which pertains to a bodily function (for example the heart rate) or a property of a person (for example the gender) and, with regard to the specific variable, contains the correlation of this variable with the probability of the suitability of this acquisition configuration for the examination. Furthermore, a probability density function that pertains to the x-ray dose to be applied to a person advantageously exists for every acquisition configuration, wherein the x-ray dose correlates with the quality of the slice images or 3D images of the heart that are reconstructed based on the acquired x-ray projections. The determination of the individual probability density functions is normally based on experimental values. A probability density function thereby does not need to exist as an analytical function; rather, they it can also exist in tabular form, for example.

If the examination type of an examination of the heart with the computed tomography apparatus is predetermined by a user, the acquisition configurations that are considered for the specified examination type are drawn from the set of adjustable acquisition configurations and the probability density functions associated with these acquisition configurations are evaluated—based on indicated, patient-specific bodily functions or properties of the variables pertaining to the patient, and/or based on an indicated value for the x-ray dose accepted for the examination by the user and to be applied to the patient—as to whether the acquisition configuration that is best suited for the examination type is determined. In this way a user can be assisted in an improved form in the adjustment of acquisition parameters.

According to one variant of the invention, the examination form to be specified is a CT angiography to acquire images of the heart for a specific cardiac phase or a CT angiography to acquire images of the heart for a specific cardiac phase and to determine the function of the heart. At least two acquisition configurations are associated with each of these examination types.

The acquisition configurations that can be adjusted at the computed tomography apparatus advantageously include at least one sequence acquisition configuration and at least one spiral acquisition configuration. Multiple sequence acquisition configurations and spiral acquisition configurations are normally present which, for example, differ in the width of the pulsing window; the position of the pulsing window in relation to the cardiac cycle of a patient; the x-ray energy to be adjusted; the pitch given a spiral acquisition configuration etc.

According to one embodiment of the invention, at least one probability density function that pertains to the heart rate, the heart rate variability, the calcium score, the age, the gender or the weight of a person is maintained for every adjustable acquisition configuration. As already mentioned, with regard to the heart rate, the heart rate variability, the calcium score etc. a probability density function indicates the correlation of these variables with the probability of the suitability of the acquisition configuration associated with this probability density function.

According to a further embodiment of the invention, the at least one determined variable to be specified that pertains to the current patient to be examined is consequently the heart rate, the heart rate variability, the calcium score, the age, the gender or the weight of the person to be examined.

According to one embodiment of the invention, a probability measure for the suitability of the respective acquisition configuration is determined that designates the acquisition configuration that is best suited for the selected examination form for every adjustable acquisition configuration under consideration, based on a normalized likelihood function with recourse to the at least one probability density function.

According to one variant of the invention, the probability measure $p_i$ is determined as follows using the Bayesian theorem for a specific, adjustable acquisition configuration under consideration:

$$p_i = \frac{L(\Theta_i \mid \vec{X})}{\sum_{k=1}^{m} L(\Theta_k \mid \vec{X})} = \frac{\prod_{j=0}^{n} f(x_j \mid \Theta_i)}{\sum_{k=1}^{m} \left[\prod_{j=0}^{n} f(x_j \mid \Theta_k)\right]}$$

It thereby applies that:

wherein $\vec{X}=(x_0, x_1, \ldots, x_n)$ is the vector of the specified, determined variables of the current patient to be examined and/or of the specified value pertaining to the x-ray dose to be applied $\Theta_i$ with $i\in(1, 2, \ldots, m)$ stands for a determined, adjustable acquisition configuration under consideration. $L(\Theta)_i \vec{X})$ is the likelihood function for the determined, adjustable acquisition configuration $\Theta_i$ under consideration of the specified, determined variables of the current patient to be examined and/or of the specified value pertaining to the x-ray dose to be applied. $f(x_j|\Theta_i)$ stands for a value of a probability density function f for a specified, determined variable of the current patient to be examined or of the specified value pertaining to the x-ray dose to be a applied for the specific, adjustable acquisition configuration $\Theta_i$ under consideration.

$$\sum_{k=1}^{m} L(\Theta_k \mid \vec{X})$$

is the sum of the likelihood functions of all adjustable acquisition configurations $\Theta_k$ in question, with $k\in(1, 2, \ldots, m)$ under consideration of the specified, determined variables of the current patient to be examined and/or of the specified value pertaining to the x-ray dose to be applied.

The sum of the probability measures $p_i$ of the adjustable acquisition configurations under consideration amounts to one $$\left(\sum_{i=1}^{m} p_i = 1\right).$$

According to one embodiment of the invention, an order of the suitability of the adjustable acquisition configuration under consideration for the specified examination type is advantageously created based on the determined probability measures $p_i$ and displayed to the user, wherein the acquisition configuration that is best suited is identified.

The object forming the basis of the invention is also achieved by a computed tomography apparatus that has a memory unit and a computer to execute one of the methods described in the preceding.

The object forming the basis of the invention is moreover achieved by non-transitory computer-readable storage medium encoded with a computer program for implementing the embodiments of the methods described in the preceding. The program can be loaded from the data medium into a computer in order to execute one of the embodiments described in the preceding when the computer program is loaded into the computer.

DESCRIPTION OF THE PREFERRED EMBODIMENTS

Figure 1:
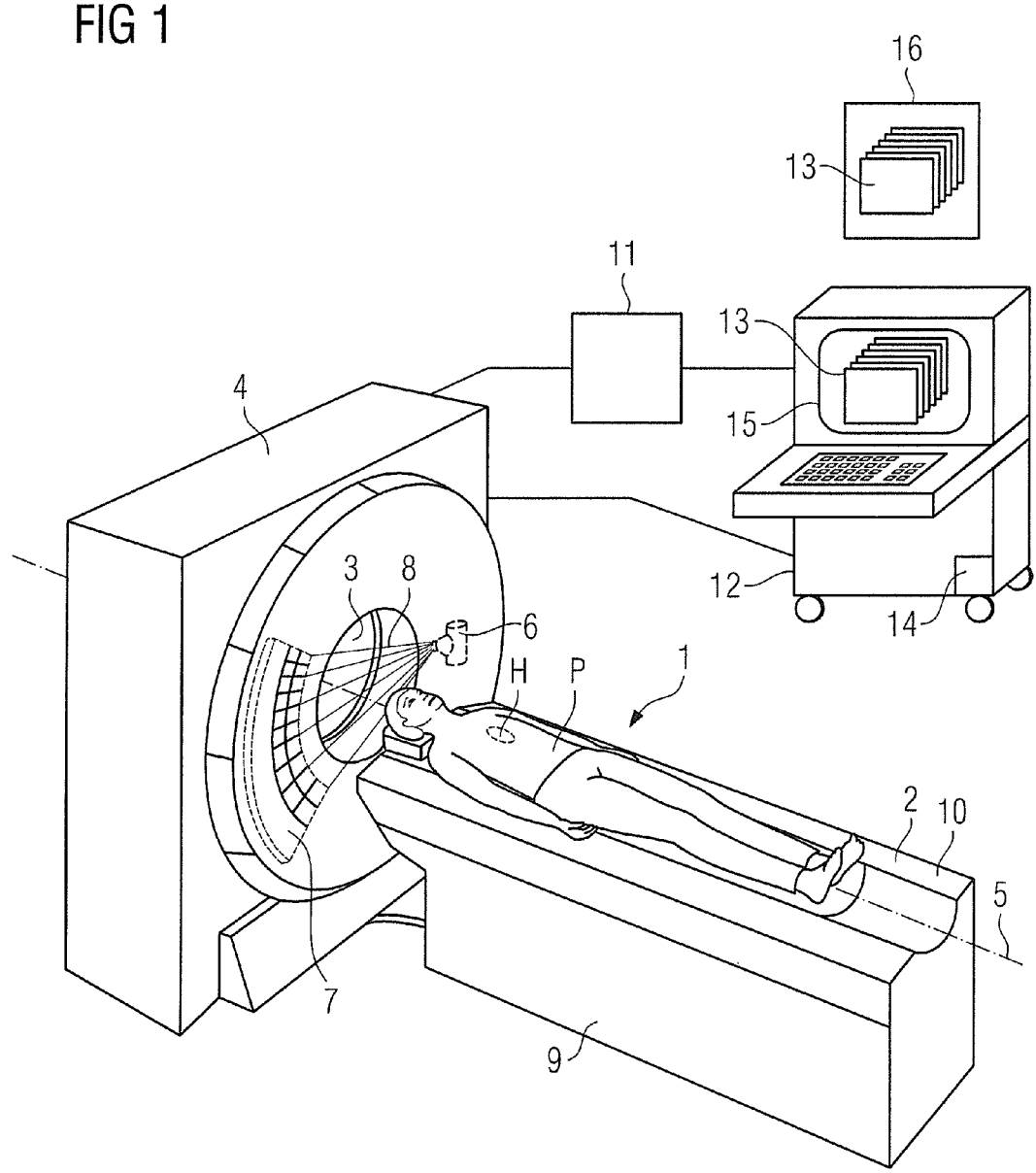
FIG. 1 shows an x-ray computed tomography apparatus.

Identical or functionally identical elements, components, tissue etc. are provided with the same reference characters throughout the figures. The depictions in figures are schematic and not necessarily true to scale, wherein scales can vary between figures. The x-ray computed tomography apparatus 1 shown in FIG. 1 is discussed in the following and without limitation of the generality only insofar as it is deemed necessary to understand the invention.

The x-ray computed tomography apparatus 1 shown in FIG. 1 has a patient bed 2 to bear a patient P to be examined. The x-ray computed tomography apparatus 1 also comprises a gantry 4 with a tube detector system borne such that it can rotate around a system axis 5. The tube detector system has an x-ray tube 6 and an x-ray detector unit 7 situated opposite one another. In operation, x-ray radiation 8 emanates from the x-ray tube 6 in the direction of the x-ray detector unit 7 and is detected by means of this.

The patient bed 2 has a bed pedestal 9 on which is arranged a patient support plate 10 provided for the actual support of the patient P. The patient support plate 10 is adjustable relative to the bed pedestal 10 such that the patient support plate 10 with the patient P can be introduced into the opening 3 of the gantry 4 to acquire 2D x-ray projections of the patient P, for example in a sequence scan or a spiral scan. The computational processing of the 2D x-ray projections—i.e. the reconstruction of slice images or of a volume data set of a body region of the patient P based on the 2D x-ray projections—ensues with a schematically depicted image computer 11 of the x-ray computed tomography apparatus 1. In the case of the present exemplary embodiment of the invention, the image computer 11 of the x-ray computed tomography apparatus 1 is connected with a computer 12 to control the x-ray computed tomography apparatus 1.

An examination of the heart H of the patient P should presently ensue with the x-ray computed tomography apparatus 1. In principle, multiple potential, suitable acquisition configurations or, respectively, scan protocols that differ however with regard to their setting parameters are provided for selection by the user of the x-ray computed tomography apparatus 1. In order to assist the user in the selection of an acquisition configuration that is suitable to achieve his goal of the examination of the heart H of the patient P, the computer 12 is provided with a corresponding computer program 13 that has presently been loaded into the computer 12 by means of a portable data medium 16 or, respectively, storage medium (for example a CD).

The computer program 13 implements a method to assist a user of the x-ray computed tomography apparatus 1 in the selection of an acquisition configuration from a set of adjustable acquisition configurations for the acquisition of 2D x-ray projections of the heart of a patient with the x-ray computed tomography apparatus 1 to examine the heart of said patient.

The computer program 13 contains (in tabular form, for example) acquisition configurations or scan protocols of the x-ray computed tomography apparatus 1 that are available in principle for various examination types or for various goals of the examination of a heart. These acquisition configurations or scan protocols are kept ready after for accessing the loading of the computer program 13 into a memory unit 14 of the computer 12. Such an association is specified as an example in the following Table 1.

| Examination type | Acquisition configuration considered for this in principle |
|---|---|
| Standard CT angiography to acquire images of the heart for a determined cardiac phase | Sequence acquisition configuration I<br>Spiral acquisition configuration I |
| CT angiography to acquire images of the heart for a determined cardiac phase and to determine the function of the heart | Sequence acquisition configuration II<br>Spiral acquisition configuration II |

Apart from the sequence mode and spiral mode, the listed sequence or spiral acquisition configurations differ in at least one of their established setting parameters, for example the width of the pulsing window, the position of the pulsing window in relation to the cardiac cycle of the patient, the tube voltage to be set, the anticipated duration of the scan, the pitch (in the case of a spiral mode), etc.

In the present exemplary embodiment of the invention, multiple probability density functions are associated with each adjustable acquisition configuration. For a specific variable pertaining to a person, such as a bodily function or a property of the person, each probability density function (associated with an acquisition configuration) of a first class of probability density functions respectively indicates the correlation of this variable with the probability of the suitability of the acquisition configuration associated with this probability density function.

In the present exemplary embodiment of the invention, a second class of probability density functions consists of only one probability density function that pertains to the x-ray dose to be applied to a person. In the present exemplary embodiment of the invention, such a probability density function indicates the correlation of the x-ray dose to be applied to a person with the probability of the suitability of the acquisition configuration associated with this probability density function. Such a probability density function is associated with each acquisition configuration. In the present exemplary embodiment of the invention, a supplementary scale from zero to ten is used for the x-ray dose, wherein zero stands for a very high image quality (and therefore for a relatively high x-ray dose) and ten stands for an adequate imaging with an optimally low x-ray dose.

The probability density functions are loaded from the data medium 16 into the memory unit 14.

Controlled by the computer program 13, the user of the x-ray computed tomography apparatus 1 is initially required to input the desired examination type or the goal of the examination of the heart H of the patient P (for example via the keyboard of the computer 12) or to select the desired examination type or, respectively, the desired goal of the examination from a provided selection (advantageously displayed on the viewing device 15 of the computer 12) of possible examination types or examination goals. In the present exemplary embodiment of the invention, a standard CT angiography to acquire images of the heart for a specific cardiac phase has been selected as the examination type.

According to the specified or selected examination type of the heart H of the patient P, in the case of the present exemplary embodiment of the invention two acquisition configurations are potentially considered according to Table 1, namely the sequence acquisition configuration I and the spiral acquisition configuration I.

For the further method the probability density functions associated with these two acquisition configurations are accordingly used. Examples of four respective probability density functions are shown in FIGS. 2 through 9 for the two acquisition configurations under consideration.

Figure 2:
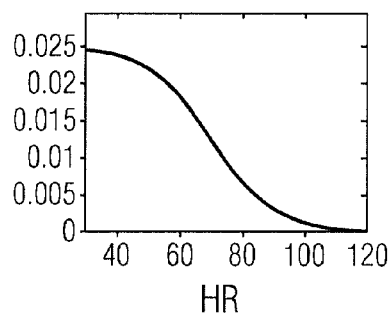
FIG. 2 through FIG. 9 show respective probability density functions.

In FIG. 2 the probability density function concerning the heart rate HR (in units of "beats per minute") of a person is shown for the sequence acquisition configuration I, which probability density function indicates the correlation between the heart rate of a person and the probability of the suitability of the sequence acquisition configuration I in relation to the heart rate.

Figure 3:
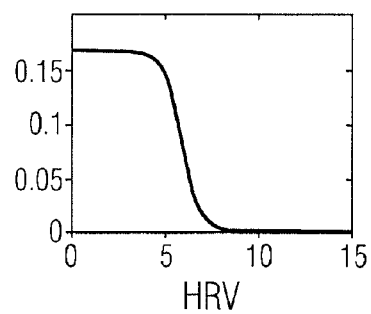
Figure 4:
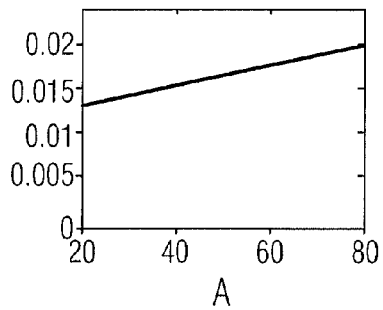
Figure 5:
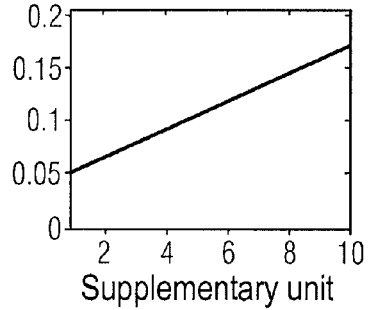

In FIGS. 3 through 5 the corresponding correlations for the heart rate variance HRV (in units of "beats per minute"), the age A (in units of "years") of a person, or the x-ray dose to be applied to a person (in the supplementary unit with the dimensionless scale from zero to ten), are shown for the sequence acquisition configuration I.

Figure 6:
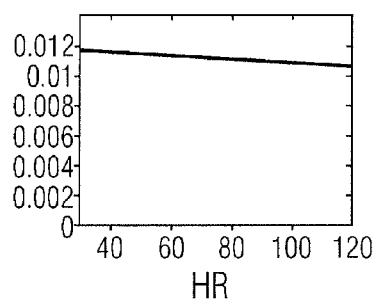

In FIG. 6 the probability density function concerning the heart rate HR (in units of "beats per minute") of a person is shown for the spiral acquisition configuration I, which probability density function again indicates the correlation between the heart rate of a person and the probability of the suitability of the spiral acquisition configuration I in relation to the heart rate.

Figure 7:
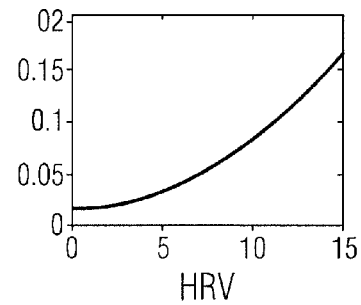
Figure 8:
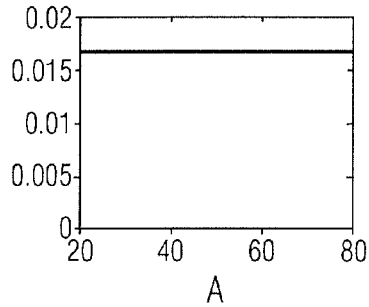
Figure 9:
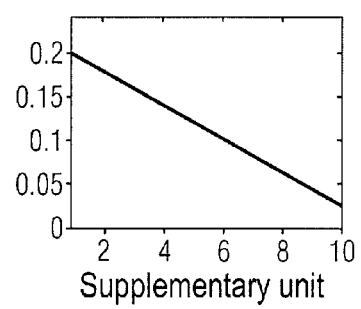

In FIGS. 7 through 9 the corresponding correlations for the heart rate variance HRV (in units of "beats per minute"), the age A (in units of "years") of a person or the x-ray dose to be applied to a person (in the supplementary unit with the dimensionless scale from zero to ten) are shown for the spiral acquisition configuration I.

In order to receive an assistance in the selection of the best-suited acquisition configuration for the examination of the patient P, the user—directed by the program—is required to specify the value $x_{HR}$ of the heart rate of the heart H of the patient P, the value $x_{HRV}$ of the heart rate variance of the heart H of the patient P and the age $x_A$ of the patient P. Moreover, the user—directed by the program—is required to input a value $x_{dose}$ between zero and ten which relates to the x-ray dose to be applied to a person. As already mentioned, the scale between zero and ten is a supplementary scale, wherein zero stands for a very high image quality and therefore the acceptance of the user that under the circumstances a relatively high x-ray dose is applied to the patient P in the acquisition of the x-ray projections. In contrast to this, ten stands for an optimally low x-ray dose being applied to the patient P for an adequate imaging. By specifying a value between zero and ten the user can thus affect whether an acquisition configuration for the examination type is suggested to him in which a relatively high x-ray dose or a relatively low x-ray dose is applied to the patient P. In the case of the present exemplary embodiment of the invention for the patient P, the vector $\vec{X}_{Patient} = (x_{HR}, x_{HRV}, x_A, x_{dose})$ can be formed from the specifications of the user.

Using the specifications of the user and the probability density functions associated with the acquisition configurations under consideration, a probability measure based on a normalized likelihood function is determined for each acquisition configuration under consideration in that ratios of likelihood functions are produced.

In the case of the present exemplary embodiment of the invention, the probability measure $p_{SequenceI}$ and $p_{SpiralI}$ are determined as follows for the two acquisition configurations in question:

$$p_i = \frac{L(\Theta_i | \vec{X})}{\sum_{k=1}^{m} L(\Theta_k | \vec{X})} = \frac{\prod_{j=0}^{n} f(x_j | \Theta_i)}{\sum_{k=1}^{m} \left[ \prod_{j=0}^{n} f(x_j | \Theta_k) \right]},$$

wherein in the case of the present exemplary embodiment of the invention it applies that:
  i∈(SequenceI=1,SpiralI=2),
  $\vec{X} = (x_0 = x_{HR}, x_1 = x_{HRV}, x_3 = x_A, x_4 = x_{dose})$ is the vector of the specified, determined variables $x_{HR}$, $x_{HRV}$, $x_A$ of the current patient P to be examined and of the specified value $x_{dose}$ pertaining to the x-ray dose to be applied, $\Theta_i$ with i∈(SequenceI=1,SpiralI=2) respectively stands for one of the two adjustable acquisition configurations under consideration, $L(\Theta_i|\vec{X})$ is the likelihood function for the determined, adjustable acquisition configuration $\Theta_i$ under consideration of the specified, determined variables $x_{HR}$, $x_{HRV}$, $x_A$ of the current patient P to be examined and of the specified value $x_{dose}$ pertaining to the x-ray dose to be applied. $f(x_j|\Theta_i)$ stands for a value of a probability density function f for a specified, determined variable $x_{HR}$, $x_{HRV}$, $x_A$ of the current patient P to be examined or of the specified value $x_{dose}$ pertaining to the x-ray dose to be applied for the a respective one of the two adjustable acquisition configurations $\Theta_i$ under consideration, $$\sum_{k=1}^{m} L(\Theta_k | \vec{X})$$

is the sum of the likelihood functions of all adjustable acquisition configurations $\Theta_k$ in question, with k∈(SequenceI=1, SpiralI=2) under consideration of the specified, determined variables $x_{HR}$, $x_{HRV}$, $x_A$ of the current patient P to be examined and of the specified value $x_{dose}$ pertaining to the x-ray dose to be applied.

$P_{SequenceI}$ accordingly results as $$p_{SequenceI} = \frac{L(\Theta_{SequenceI} | \vec{X}_P)}{L(\Theta_{SequenceI} | \vec{X}_P) + L(\Theta_{SpiralI} | \vec{X}_P)} = \frac{\prod_{j=0}^{4} f(x_j | \Theta_{SequenceI})}{\sum_{k=1}^{2} \left[ \prod_{j=0}^{4} f(x_j | \Theta_k) \right]}$$

and $p_{SpiralI}$ accordingly results as $$p_{SpiralI} = \frac{L(\Theta_{SpiralI} | \vec{X}_P)}{L(\Theta_{SequenceI} | \vec{X}_P) + L(\Theta_{SpiralI} | \vec{X}_P)} = \frac{\prod_{j=0}^{4} f(x_j | \Theta_{SpiralI})}{\sum_{k=1}^{2} \left[ \prod_{j=0}^{4} f(x_j | \Theta_k) \right]}$$

The values of the probability density functions that are required to calculate the probability measures $p_{SequenceI}$ and $p_{SpiralI}$ are respectively taken from the probability density functions shown in FIGS. 2 through 9 using the values $\vec{X}_{Patient} = (x_{HR}, x_{HRV}, x_A, x_{dose})$ specified by the user.

Based on the calculated values of the probability measures $p_{SequenceI}$ and $p_{SpiralI}$, an order of the suitability of the two adjustable acquisition configurations (sequence acquisition configuration I and spiral acquisition configuration I) in question is obtained, wherein the acquisition configuration best suited for the selected examination type of the patient P is identified in that this is correspondingly presented on the viewing device 15, for example.

The acquisition configuration that is determined as being the best-suited acquisition configuration can either be set automatically or be offered to the user for selection.

In contrast to the described exemplary embodiment of the invention, more than two acquisition configurations for an examination type of a heart of a patient can also be considered.

Furthermore, more than the four described probability density functions can be associated with each acquisition configuration, which probability density functions additionally concern the gender, the weight or the calcium score of the patient, for example.

The user can be permitted to make a selection as to which probability density functions are used for the determination of the probability measures. Such a selection is best made via a provided selection list.

If the order of the suitability of the acquisition configurations is determined, problematic or, respectively, less well-suited acquisition configurations can be accordingly identified or even blocked from the selection.

In the present exemplary embodiment of the invention, the x-ray computed tomography apparatus 1 has only one x-ray system with one x-ray source and one x-ray receiver. However, the invention also concerns x-ray computed tomography apparatuses with two or even more x-ray systems.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computerized method to assist configuring a computed tomography (CT) apparatus to an adjustable acquisition configuration among a plurality of available adjustable acquisition configurations, to implement an examination of the heart of a patient, comprising the steps of:

prior to implementing an examination of the heart of a patient with a CT apparatus, entering information into a computerized processor that designates a patient-specific variable of the patient and an x-ray dose-specific variable of the examination;

in a memory accessible by said processor, storing and associating with, for each of said available adjustable acquisition configurations, at least two probability density functions, with a first of said at least two probability density functions generally correlating a patient variable with a probability of suitability of the associated adjustable acquisition configuration, and with a second of said at least two probability density functions generally correlating an x-ray dose with a probability of suitability of the associated adjustable acquisition configuration;

in said processor, accessing said probability density functions respectively for at least two of the available adjustable acquisition configurations and, for each of the first and second probability density functions associated therewith, determining the respective probability of suitability of the associated adjustable acquisition configuration for the patient-specific variable and for the x-ray dose-specific variable and, from the determined probabilities, selecting one of said at least two of said adjustable acquisition configurations for use in implementing said examination of said patient; and providing an indication of the selected adjustable acquisition configuration at an output of the processor in a form allowing the CT apparatus to be configured according to the selected adjustable acquisition configuration.

2. A method as claimed in claim 1, comprising providing said information to said computerized processor for a CT angiography procedure to acquire images of the heart of the patient for a predetermined cardiac phase.

3. A method as claimed in claim 1, comprising providing said information to said computerized processor for a CT angiography procedure to acquire images of the heart of the patient for a predetermined cardiac phase and to determine functioning of the heart.

4. A method as claimed in claim 1 comprising, from said processor, accessing respective probability functions for at least one sequence acquisition configuration and at least one spiral acquisition configuration, as said at least two of said available adjustable acquisition configurations.

5. A method as claimed in claim 1 comprising storing in said memory, for each of said available adjustable acquisition configurations, a probability density function, as said first of said at least two probability density functions, selected from the group consisting of a probability density function pertaining to heart rate, a probability density function pertaining to heart rate variability, a probability density function pertaining to calcium score, a probability density function pertaining to patient age, a probability density function pertaining to patient gender, and a probability density function pertaining to patient weight.

6. A method as claimed in claim 5 comprising designating, as said patient-specific variable of said patient, a designation selected from the group consisting of the patient's heart rate, the patient's heart rate variability, the patient's calcium score, the patient's age, the patient's gender, and patient's weight.

7. A method as claimed in claim 1 comprising, in said processor, calculating a probability measure representing the suitability of each of said at least two adjustable acquisition configurations accessed by said processor based on a normalized likelihood function using said at least one probability density function.

8. A method as claimed in claim 7 comprising calculating the probability measure $p_i$ as follows for a specific, adjustable acquisition configuration under consideration:

$$p_i = \frac{L(\Theta_i \mid \vec{X})}{\sum_{k=1}^{m} L(\Theta_k \mid \vec{X})} = \frac{\prod_{j=0}^{n} f(x_j \mid \Theta_i)}{\sum_{k=1}^{m} \left[\prod_{j=0}^{n} f(x_j \mid \Theta_k)\right]}$$

wherein $\vec{X}=(x_0, x_1, \ldots, x_n)$ is the vector of the specified, determined variables of the current patient to be examined and/or of the specified value pertaining to the x-ray dose to be applied, $\Theta_i$ with $i\epsilon(1, 2, \ldots, m)$ stands for a determined, adjustable acquisition configuration under consideration, $L(\Theta_i \mid \vec{X})$ is the likelihood function for the determined, adjustable acquisition configuration $\Theta_i$ under consideration of the specified, determined variables of the current patient to be examined and/or of the specified value pertaining to the x-ray dose to be applied, $f(x_j \mid \Theta_i)$ stands for a value of a probability density function f for a specified, determined variable of the current patient to be examined or of the specified value pertaining to the x-ray dose to be a applied for the specific, adjustable acquisition configuration $\Theta_i$ under consideration, and $$\sum_{k=1}^{m} L(\Theta_k \mid \vec{X})$$

is the sum of the likelihood functions of all adjustable acquisition configurations $\Theta_k$ in question, with $k\epsilon(1, 2, \ldots, m)$ under consideration of the specified, determined variables of the current patient to be examined and/or of the specified value pertaining to the x-ray dose to be applied.

9. A method as claimed in claim 1 comprising providing, as said indication of the selected adjustable acquisition configuration at the output of the processor, a humanly perceptible indication of the respective suitabilities of each of said at least two of said available adjustable acquisition configurations accessed by said processor.

10. A computed tomography (CT) apparatus, comprising:
a CT data acquisition unit that interacts with a patient to acquire CT data from the patient in an examination of the heart of the patient, said CT data acquisition unit being operable in an adjustable acquisition configuration from among a plurality of available adjustable acquisition configurations;
a computerized processor configured to receive as an input, prior to implementing said examination of the heart of a patient, information that designates a patient-specific variable of the patient and an x-ray dose-specific variable of the examination;
in a memory accessible by said processor in which, for each of said available adjustable acquisition configurations, at least two probability density functions are stored and associated respectively with the at least two probability density functions, with a first of said at least two probability density functions generally correlating a patient variable with a probability of suitability of the associated adjustable acquisition configuration, and with a second of said at least two probability density functions generally correlating an x-ray dose with a probability of suitability of the associated adjustable acquisition configuration;

said processor being configured to access said probability density functions respectively for at least two of the available adjustable acquisition configurations and, for each of the first and second probability density functions associated therewith, determine the respective probability of suitability of the associated adjustable acquisition configuration for the patient-specific variable and for the x-ray dose-specific variable and, from the determined probabilities, select one of said at least two of said adjustable acquisition configurations for use in implementing said examination of said patient; and provide an indication of the selected adjustable acquisition configuration at an output of the processor in a form allowing the CT apparatus to be configured according to the selected adjustable acquisition configuration.

11. A non-transitory computer-readable storage medium encoded with programming instructions, said medium being loaded into a computerized operating system of a computed tomography (CT) apparatus, said CT apparatus being operable in an adjustable acquisition configuration from among a plurality of available adjustable acquisition configurations, and said programming instructions causing said computerized operating system to:

prior to implementing said examination of the heart of a patient with a CT apparatus, receive information into a processor of said computerized operating system that designates a patient-specific variable of the patient and an x-ray dose-specific variable of the examination;

in a memory accessible by said processor, store and associate with, for each of said available adjustable acquisition configurations, at least two probability density functions, with a first of said at least two probability density functions generally correlating a patient variable with a probability of suitability of the associated adjustable acquisition configuration, and with a second of said at least two probability density functions generally correlating an x-ray dose with a probability of suitability of the associated adjustable acquisition configuration;

in said processor, access said probability density functions respectively for at least two of the available adjustable acquisition configurations and, for each of the first and second probability density functions associated therewith, determine the respective probability of suitability of the associated adjustable acquisition configuration for the patient-specific variable and for the x-ray dose-specific variable and, from the determined probabilities, select one of said at least two of said adjustable acquisition configurations for use in implementing said examination of said patient; and provide an indication of the selected adjustable acquisition configuration at an output of the processor in a form allowing the CT apparatus to be configured according to the selected adjustable acquisition configuration.

* * * * *